United States Patent [19]

[11] 4,379,145

Masuho et al.

[45] Apr. 5, 1983

[54] ANTITUMOR PROTEIN HYBRID AND PROCESS FOR THE PREPARATION THEREOF

[75] Inventors: Yasuhiko Masuho; Naoji Umemoto, both of Hino; Takeshi Hara, Hachioji; Hidematsu Hirai, Sapporo, all of Japan

[73] Assignees: Teijin Limited, Osaka; Hidematsu Hirai, Hokkaido, both of Japan

[21] Appl. No.: 216,709

[22] Filed: Dec. 15, 1980

[30] Foreign Application Priority Data

Dec. 14, 1979 [JP] Japan ................................ 54-161609

[51] Int. Cl.[3] .................... A61K 37/00; C07C 103/52; C07G 7/00

[52] U.S. Cl. ............................ 424/177; 260/112.5 R; 260/112 R

[58] Field of Search .................... 260/112.5 R, 112 R; 424/177

[56] References Cited

FOREIGN PATENT DOCUMENTS 17507 10/1980 European Pat. Off. ..... 260/112.5 R

OTHER PUBLICATIONS

F. L. Moolten, et al., J. National Cancer Inst., Aug. 1975, vol. 55, No. 2.

Moolten et al., J. of the National Cancer Inst., 1975, vol. 55, No. 3, pp. 709–712.

Boquet; Biochem. and Biophys. Res. Commun. 75, No. 3, 1977, 696–702.

*Primary Examiner*—Delbert R. Phillips

*Attorney, Agent, or Firm*—Sughrue, Mion, Zinn, Macpeak and Seas

[57] ABSTRACT

Antitumor protein hybrid, having a moiety consisting of the antitumor immunoglobulin and a moiety substantially consisting of the fragment A of a diphtheria toxin, which is expressed by the following formula (I):

$$Ab(NHCO-X-S_1-S_2-FA)_n \quad (I)$$

(where Ab indicates a moiety consisting of the antitumor immunoglobulin and FA indicates a moiety substantially consisting of the fragment A of a diphtheria toxin; X is an alkylene group or phenylene group which either has or does not have a branching of 1 to 5 carbon atoms. N in the amido bond is a nitrogen atom arising from the amino group in the antitumor immunoglobulin; $S_1$ and $S_2$ are both sulfur atoms, $S_2$ indicating a sulfur atom arising from the disulfide bond in a diphtheria toxin; n stands for an integer of 1 to 5).

This antitumor protein hybrid has remarkable and specific citotoxicity against tumor cells.

4 Claims, 6 Drawing Figures

ANTITUMOR PROTEIN HYBRID AND PROCESS FOR THE PREPARATION THEREOF

BACKGROUND OF THE INVENTION

1. Field of the Invention

The present invention relates to a novel antitumor protein hybrid and a process for the preparation thereof. More particularly, the present invention relates to a novel protein hybrid, specifically useful as a remedy for malignant tumor, which has a moiety consisting of the antitumor immunoglobulin and a moiety substantially consisting of the fragment A of a diphtheria toxin, and a process for the preparation of the same.

2. Description of the Prior Art

Many drugs (anti-cancer agents) have hitherto been known to cure malignant tumor or cancer; however, since these drugs display considerable toxicity not only to tumor cells but also to normal cells, they can not be administered in doses large enough to perish tumor cells, which is their inherent demerit. To correct such demerit, several attempts have been made, wherein an anti-cancer agent or cytotoxic protein toxin is conjugated to a special carrier to make it attractive to tumor cells selectively. There exists an antitumor antibody (antitumor immunoglobulin), though very small in amount, in the blood or on the surface of tumor cells of a cancer patient. The antitumor antibody has hitherto been practically been obtained by first immunizing an animal with the cancer tissue and then absorbing the obtained antiserum with the normal tissue of a human being. Antitumor antibodies, whether autochthonous, allogenic, or xenogenic, do not necessarily display a cytotoxic effect against tumor cells; however, they have a common nature of binding to cancer cells with an extremely high selectivity. Antitumor antibodies have, therefore, been utilized as a carrier to make an anti-cancer agent or protein toxin bind to tumor cells selectively.

For instance, U.S. Pat. No. 4093607 discloses an antitumor drug comprising an antibody-drug conjugate in which an anti-cancer agent such as daunomycin, etc. is covalently bonded to the Fab' dimer of an antitumor immunoglobulin. This conjugate is a good one in respect of a fact that it binds the drug to a target tumor cell with some selectivity. But, in general, as the anti-cancer agent such as daunomycin, etc., when liberated from the conjugate prior to its entry to the cell, displays cytotoxicity not only against tumor cells but also against normal cells, it does not work satisfactorily in terms of efficacy to destroy tumor cells only. Moreover its cytotoxicity is not completely strong, either.

Studies have also been made as to the use of a diphtheria toxin, one of the protein toxins which are much stronger in cytotoxicity, in the place of an anti-cancer agent.

For instance, F. L. Moolten et al. report that they prepared a conjugate by conjugating a rabbit anti-SV40 antibody to a diphtheria toxin with glutaraldehyde as coupling agent and were able to protect hamsters challenged with SV40-transformed 3T3 cells by administering the conjugate to the hamsters (Journal of the National Cancer Institute, vol. 55, pp. 473–477, 1975).

P. E. Thorpe et al. report that a conjugate prepared by coupling a diphtheria toxin to an antilymphocytic antibody by means of chlorambucil greatly inhibited the protein synthesis of human lymphoblastoid cells, CLA4 (Nature, Vol. 271, pp. 752–754, 1978).

These studies show that a conjugate of diphtheria toxin and antibody displays toxicity against the tumor cells selectively. However, these conjugates, when used as an antitumor drug, are supposed to have some demerits as mentioned below. The first of the demerits is that the nonspecific toxicity of diphtheria toxin is not nullified. More particularly, the object of these methods is to concentrate diphtheria toxin on the surface of tumor cells by the aid of antitumor antibody; however, since the conjugate contains the whole molecule of diphtheria toxin in its composition, it is apt to bind to normal cell surface receptors for diphtheria toxin and display cytotoxicity against normal cells. The second of the demerits is found with the method of crosslinking the antibody with the diphtheria toxin. Many of the cross-linking agents such as glutaraldehyde, toluene diisocyanate, chlorambucil, etc. effect the cross-linking not only between the antibody and the toxin but also between the antibody and the antibody, and the toxin and the toxin, and moreover, they effect the formation of intramolecular bonds in the antibody and in the toxin molecule, thus causing the formation of undesirable products and decrease or loss of the antitumor activity.

SUMMARY OF THE INVENTION

The present inventors have achieved this invention as a result of the earnest research work to develop an antitumor substance which displays strong and selective cytotoxicity against tumor cells.

The present invention relates to an antitumor protein hybrid, having a moiety consisting of the antitumor immunoglobulin and a moiety which is substantially the fragment A of a diphtheria toxin, which is expressed by the following formula (I):

$$Ab\text{-}(NHCO-X-S_1-S_2-FA)_n \qquad (I)$$

(where Ab indicates a moiety consisting of the antitumor immunoglobulin and FA indicates a moiety substantially consisting of the fragment A of a diphtheria toxin; X is an alkylene group or phenylene group which either has or does not have a branching of 1 to 5 carbon atoms; N in the amido bond is a nitrogen atom arising from the amino group in the antitumor immunoglobulin; $S_1$ and $S_2$ are both sulfur atoms, $S_2$ indicating a sulfur atom arising from the disulfide bond in a diphtheria toxin; n stands for an integer of 1 to 5), and a process for preparing the antitumor protein hybrid, which process comprises binding the antitumor immunoglobulin and the fragment A of a diphtheria toxin with a cross-linking agent.

DESCRIPTION OF THE PREFERRED EMBODIMENTS

What is called an antitumor immunoglobulin in the present invention is a protein (immunoglobulin) having an antibody activity prepared, for instance, from the serum of patients with cancer or the serum obtained from such animals as monkeys, horses, cows, goats, sheep, rabbits, etc. which are hyperimmunized with tumor cells, tumor specific antigens or tumor associated antigens such as an α-fetoprotein (AFP) and carcinoembryonic antigen (CEA) according to a publicly known method such as Cohn ethanol fractionation method, ammonium sulfate fractionation method, ion-exchange chromatography method, etc., or is a protein having an antibody activity of very remarkable singularity prepared from the culture fluid of hybridomas or from serum and ascites obtained from animals inoculated with hybridomas, which are cultivable and also producible of an antibody, prepared by fusing the antibody producing lymphocytes, which are obtained by immunizing an animal with tumor cells or tumor antigen, with tumor cells (myelomas). A protein, which has an antibody activity, prepared according to the same method as mentioned above from an antitumor antibody liberated from tumor tissues with the use of such a denaturant as surface-active agent, etc. also belongs to the antitumor immunoglobulin of the present invention. A moiety of antitumor immunoglobulin which constitutes one of the moieties which make up the antitumor protein hybrid of the present invention means a moiety which comprises the aforementioned immunoglobulin. Since this type of immunoglobulin has in its molecule a plurality of amino groups arising from terminal amino groups or lysines of the constituent amino acids, such amino groups are utilized for the preparation of the antitumor protein hybrid of the present invention. The number of amino groups to be utilized should preferably be in the range of 1 to 5 (which corresponds to $n=1$ to 5 in formula (I)).

Figure 1:
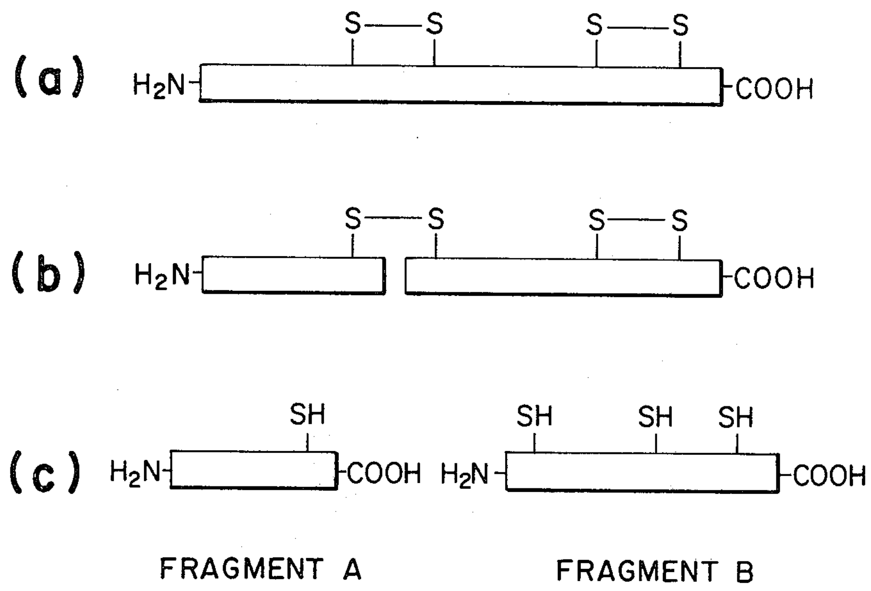
FIG. 1 is a pictorial drawing of a type specimen to show a diphtheria toxin and its fragments, in which (a) shows a structure of an intact toxin, (b) that of a nicked toxin, and (c) those of a fragment A and a fragment B.

What is called diphtheria toxin in the present invention is a protein toxin produced by Corynebacterium diphtheriae or its mutants. For instance, a diphtheria toxin produced by Corynebacterium diphtheria consists of a single polypeptide chain having a molecular weight of about 62,000 to 63,000 and this is called an intact toxin. The intact toxin has two disulfide bonds (—S—S— bonds) in its molecule as shown in a pictorial drawing of a type specimen of FIG. 1, (*a*). When this intact toxin is treated under moderate conditions with such a proteolytic enzyme as trypsin, there occures a cleavage at a specific point in the peptide chain connected with the disulfide bond somewhat nearer to the amino-terminal to form a nicked toxin as shown in FIG. 1, (*b*). When this nicked toxin is directly treated with a reducing agent or treated with a reducing agent after it is cleaved by means of sulfonation with sulfite ions, it is divided into fragment A having a molecular weight of about 24,000 and fragment B having a molecular weight of about 38,000 to 39,000 as shown in FIG. 1, (*c*). The intact toxin and nicked toxin have a very strong toxicity against animals; however, fragment A and fragment B themselves are both nontoxic. On the other hand, the intact toxin and nicked toxin have no adenosine diphosphate (ADP)-ribose transferase activity on the elongation factor 2 (EF-2) defined below, while fragment A has the transferase activity. And though fragment B has no transferase activity, it has the capability of coupling to a cell receptor which fragment A does not have.

In the present invention, the moiety substantially comprising fragment A which makes one of the moieties of the antitumor protein hybrid means a moiety composed of a fragment of the diphtheria toxin which satisfies the aforementioned characteristics of fragment A, namely the following two characteristics:

(1) To have ADP-ribose transferase activity on EF-2.

(2) To have no capability of coupling to a cell receptor and no cytotoxicity by itself.

So far as the above mentioned two requirements are satisfied, nontoxic protein produced by mutant (which has one disulfide bond in the molecule) such as CRM 30 and CRM 45 produced, for instance, from such *Corynebacterium diphtheriae* mutant as $C_7$ (β30) and $C_7$ (β45) and fragments obtained by treating them under moderate conditions with trypsin in the presence of such a reducing agent as thiol reagent are included in fragment A of the present invention.

Fragment A thus obtained is used for the preparation of antitumor protein hybrid of the present invention just as it is without being subjected to any treatment when it has at least one thiol radical in the fragment. When it has one disulfide bond in the fragment, it is used after having been made into a fragment having at least one thiol radical by cleaving the disulfide bond according to a publicly known method. As for fragment A in the present invention, a fragment having one thiol radical in the molecule is especially preferable.

Incidentally, the ADP-ribose transferase activity on EF-2 is defined as follows.

EF-2 is known as a protein elongation factor which is related with protein synthesis of cells, and fragment A of the diphtheria toxin deactivates EF-2 by catalytically promoting the reaction mentioned below between EF-2 and nicotinamide-adeninedinucleotide (NAD):

$$EF\text{-}2+NAD^+ \rightarrow (ADP\ ribose)\text{—}(EF\text{-}2)+nicotinamide+H^+$$

The performance to promote this reaction is defined as ADP-ribose transferase activity on EF-2.

ADP-ribose transferase activity on EF-2 acts to interfere with protein synthesis and works as entity of the lethal toxicity for animals; however, it is necessary for the fragment A of a diphtheria toxin which has this ADP-ribose transferase activity on EF-2 to have fragment B which is capable of coupling to a cell-receptor in order to make fragment A enter into the cell and exert its cytocidal effect: fragment A alone can not bring animals to death.

The antitumor protein hybrid of the present invention expressed by the aforementioned formula (I) is obtained by bonding said antitumor immunoglobulin and fragment A with a cross-linking agent. A cross-linking agent used in the present invention has an alkylene group or phenylene group either having or not having a branch of 1 to 5 carbon atoms as a primary component (corresponding to X in the aforementioned formula (I)), additionally having one active ester group and one active disulfide group. An ethylene group is especially preferable as the primary component. Of the cross-linking agents, the active ester group reacts with the amino group of the immunoglobulin to form an amide bond and the active disulfide group reacts with the thiol group of the fragment A to form a new disulfide bond, thus providing the antitumor protein hybrid expressed by the aforementioned formula (I). In the present invention, preferable cross-linking agents are compounds expressed by the following formula (II):

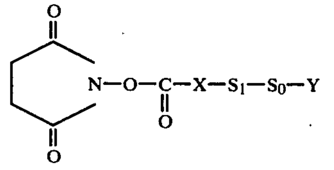

(II)

(where X is an alkylene group or phenylene group either having or not having a branch of 1 to 5 carbon atoms. Y indicates

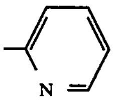

or

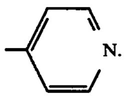

Both $S_I$ and $S_O$ indicate atoms of sulfur).

Some of the compounds included in the above formula (II) are mentioned concretely hereunder:

N—succinimidyl 2-(2-pyridyldithio)acetate
$(X = -CH_2-)$,

N—succinimidyl 3-(2-pyridyldithio)propionate
$(X = -(CH_2)_2-)$,

N—succinimidyl 3-(4-pyridyldithio)propionate
$(X = -(CH_2)_2-)$,

N—succinimidyl 4-(2-pyridyldithio)butylate
$(X = -(CH_2)_3-)$,

N—succinimidyl 3-(2-pyridyldithio)valerate
$(X = -\underset{C_2H_5}{\underset{|}{C}}HCH_2-)$, N—succinimidyl 4-(2-pyridyldithio)valerate
$(X = -\underset{CH_3}{\underset{|}{C}}HCH_2CH_2-)$ N—succinimidyl 5-(2-pyridyldithio)valerate
$(X = -(CH_2)_4-)$, N—succinimidyl 5-(4-pyridyldithio)valerate
$(X = -(CH_2)_4-)$, N—succinimidyl m-(2-pyridyldithio)benzoate (X = 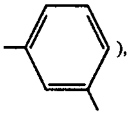 ), etc. may be mentioned. Of these compounds mentioned above, N-succinimidyl 3-(2-pyridyldithio)propionate, for instance, can be obtained by first reacting 3-mercaptopropionic acid with 2,2'-dipyridyldisulfide in a proper solvent and then by reacting the obtained reaction product with N-hydroxysuccinimide in the presence of a condensing agent (See the Biochemical Journal, Volume 173 (1978) pp. 723–737).

The antitumor protein hybrid of the present invention is obtained, as mentioned in the foregoing, by reacting the antitumor immunoglobulin with the substantial fragment A of a diphtheria toxin and a cross-linking agent which has one active ester group and one active disulfide group in the molecule. No specific limit is placed upon the order, method, etc. of the reaction. However, a method, in which 1 to 5 amino groups of the antitumor immunoglobulin are first made to react with a cross-linking agent and then thus obtained reaction product is made to react with the substantial fragment A of a diphtheria toxin which has at least one thiol group in the fragment, is a preferable one.

The reaction between the antitumor immunoglobulin and the cross-linking agent is conducted by adding the cross-linking agent dissolved in a small amount of solvent such as methanol, ethanol, acetone, etc. (preferably ranging in concentration from 5 to 40 m M, or at a ratio of 1 mole of the former per 1 to 40 moles of the latter) to a buffer solution of antitumor immunoglobulin with pH ranging from 5 to 9 (preferably to be prepared to have the protein concentration of 0.5 to 100 mg/ml, or more preferably in the range of 1 to 20 mg/ml) at 0° to 40° C. with stirring for 15 minutes to 12 hours. Thereafter, the reaction mixture is subjected to gel filtration or dialysis to remove the cross-linking agent left still unreacted and reaction products of low molecular weight. The successive reaction is conducted at 0° to 40° C. for 15 minutes to 12 hours by adding a buffer solution (the preferable protein concentration being in the same range as mentioned above) of fragment A (having at least one thiol group) of a diphtheria toxin with pH ranging from 5 to 9 to a solution of thus obtained reaction product-protein in which 1 to 5 cross-linking agents are bonded to antitumor immunoglobulin with amide groups. The separation of the hybrid obtained by the method, which comprises the antitumor immunoglobulin and fragment A, from the reaction mixture and purification thereof can be conducted by means of an ordinary process such as molecular sieve chromatography.

The antitumor protein hybrid of the present invention has a moiety substantially consisting of the fragment A which demonstrates toxicity against tumor cells and a moiety consisting of the antitumor immunoglobulin which specifically recognizes the tumor cell and works as a carrier to guide the fragment A to the tumor cell and make the fragment A taken into the cell as well, and this hybrid has excellent characteristics mentioned below.

(1) In the hybrid of the present invention, the immunoglobulin substantially retains its original form and, therefore, the ability of the antitumor immunoglobulin to selectively couple to tumor cells and its performance to activate complements remain intact.

(2) It is known that, in case of diphtheria toxin, it is the fragment B that has the nature to couple to the receptor of cells (both normal cells and tumor cells) and that the fragment A is taken into the cell by means of the coupling of the fragment B to the cell membrane to demonstrate the cytotoxicity. However, since the hybrid of the present invention does not contain the fragment B, the hybrid of the present invention does not demonstrate the cytotoxicity to normal cells. Furthermore, since it does not contain the fragment B, the antigenicity of a diphtheria toxin is also reduced.

(3) The hybrid of the present invention has a moiety consisting of the antitumor immunoglobulin, and this moiety specifically recognizes a tumor cell and makes the tumor cell specifically take in the moiety substantially consisting of the fragment A of the diphtheria toxin. The fragment A thus taken in demonstrates a remarkable cytotoxicity to the tumor cell.

The present invention is described in detail by the following examples.

EXAMPLE 1

(a) PREPARATION OF RABBIT ANTI-AH 66 ANTIBODY 70 ml of anti-serum was obtained from three rabbits hyperimmunized with rat hepatoma cells AH 66. The anti-serum was inactivated (being treated at 56° C. for 30 minutes), to which ammonium sulfate was added (40% saturation) to precipitate immunoglobulin (IgG). The precipitation thus formed was separated by means of centrifugation. The obtained precipitate was dissolved in a 10 m M phosphate buffer (pH 7.8) and was dialyzed against the same buffer. Thus obtained solution of immunoglobulin was subjected to DEAE cellulose chromatography (column capacity, 130 ml) to obtain a solution of phosphate buffer which contained about 100 mg of IgG as a fraction not adsorbed. The obtained IgG contained the anti-AH 66 antibody and was almost homogeneous in SDS-polyacrylamide gel electrophoresis.

(b) PREPARATION OF FRAGMENT A OF DIPHTHERIA TOXIN 0.15 ml of a trypsin solution having the concentration of 0.1 mg/ml was added to 18.5 ml of 0.05 M Tris.HCl-2 m M ethylenediaminetetraacetic acid aqueous solution (pH 8.3) containing 210 mg of diphtheria toxin, and the digestion was carried out at 25° C. for 50 minutes. After that, 0.3 ml of a soybean trypsin inhibitor solution having the concentration of 0.5 mg/ml was added thereto to stop the reaction. Urea (final concentration of 6 M), sodium sulfite (final concentration 0.168 M) and sodium tetrathionate (final concentration 0.042 M) were added to the obtained digestion product and the mixture was subjected to S-sulfonative cleavage at 37° C. for 2 hours. The resulting reaction solution was put to Sephadex G150 column chromatography (column size 3.5 cm×112 cm) over a solution (pH 5.3) of 6 M urea-0.03 M acetate buffer and the fractions of fragment A which come out later were collected. These fractions were dialyzed against distilled water to give a pure fragment A solution (having one S-sulfo radical).

The S-sulfonated fragment A (about 6 mg) thus obtained was treated in a solution (pH 8.3) of 20 m M Tris.HCl buffer which contained 2 m M 2-mercaptoethanol and 0.5 m M ethylenediaminetetraacetic acid at 37° C. for 1 hour. The solution was then subjected to the gel filtration on Sephadex G 25 column (column size: 1 cm×44 cm) over a solutin (pH 5.5) of 5 m M acetate buffer containing 0.1 M sodium chloride and 1 m M ethylenediaminetetraacetic acid to obtain fragment A having one thiol group.

(c) PREPARATION OF ANTITUMOR PROTEIN HYBRID 0.6 ml of a solution (pH 7.5) of 0.3 M sodium chloride 0.3 M phosphate buffer and 0.05 ml of a 10 m M ethanol solution of N-succinimidyl 3-(2-pyridyl dithio)propionate were added to 1.2 ml of a solution of anti-AH 66 immunoglobulin (5.94 mg/ml) obtained in the aforementioned (a) to make them react with each other at 23° C. with occasional shaking for 45 minutes. The reaction solution was subjected to the gel filtration on Sephadex G25 column (column size: 0.8 cm×3.9 cm) over a solution (pH 7.5) of 0.1 M sodium chloride 0.1 M phosphate buffer to eliminate excess reagent and reaction products of low molecular weight.

The number of the cross-linking agents introduced into one molecule of the immunoglobulin was obtained by first reducing an aliquot of the mixture by adding (1/20) part by volume of a 0.4 M Tris.HCl buffer (pH 8.3) containing 10 m M ethylenediaminetetraacetic acid and (1/20) part by volume of 0.5 M 2-mercaptoethanol and then by determining the concentration of the liberated pyridine-2-thione by measuring the absorbance at 343 nm. The result of the measurement showed that an average of 5 cross-linking agents were introduced into one molecule of immunoglobulin.

Figure 2:
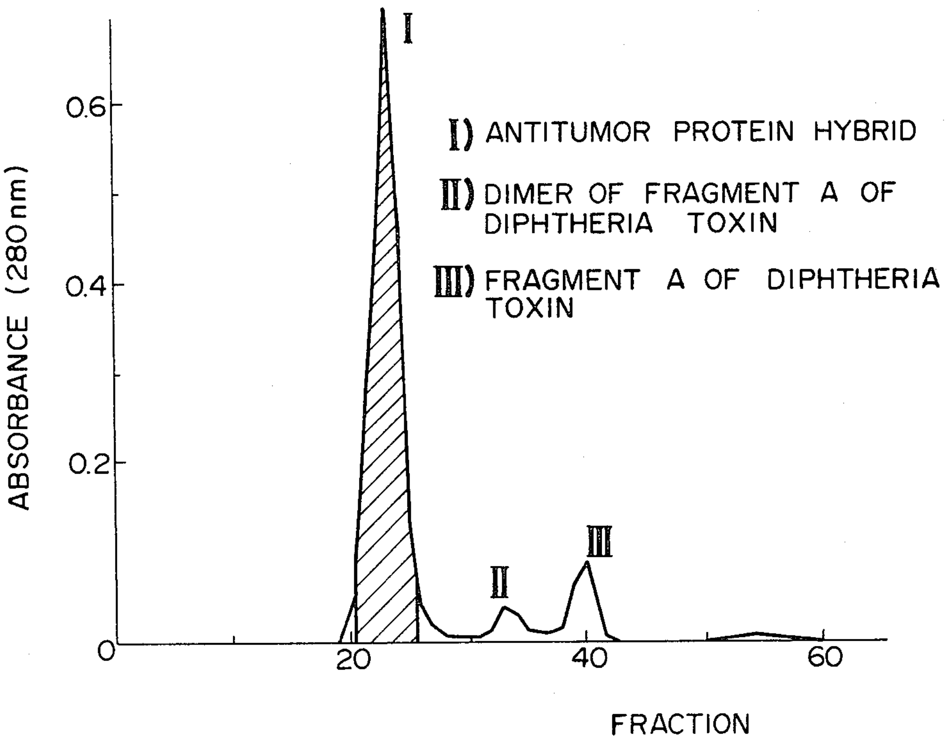
FIG. 2 shows the elution pattern of a reaction product of the anti-AH 66 immunoglobulin, into which the 3-(2-pyridyldithio) propinyl groups are introduced by amide bonds, and the fragment A of a diphtheria toxin on Sephadex G 150 superfine column chromatography and the shadowed portion shows where the hybrid of the present invention is eluted.

1.5 ml of a solution of the fragment A of a diphtheria toxin (1.07 mg/ml) which was prepared in the foregoing (b) was added to 1.7 ml of a solution of anti-AH 66 immunoglobulin (2.82 mg/ml) into which cross-linking agents containing active disulfide groups were introduced by amide bonds. After the mixture was left standing at 0° C. for 1 hour, it was dialyzed overnight at room temperature (18° to 23° C.) against 1 l of 0.1 M sodium chloride 0.1 M phosphate buffer (pH 7.5). Unreacted fragment A of a diphtheria toxin, reaction products of low molecular weight and small amount of dimers of fragment A generated during the reaction were removed on Sephadex G 150 superfine column chromatography (column size: 1.6 cm×93 cm) over 0.9% sodium chloride to obtain about 6 mg of antitumor protein hybrid. (See FIG. 2) When this hybrid was subjected to gel precipitation reaction against horse anti-diphtheria toxin antiserum and sheep anti-rabbit IgG anti-serum, precipitin lines were formed in respective cases and these precipitin lines united together, from which it was confirmed that the hybrid was an antibody-toxin hybrid.

(d) ANTITUMOR ACTIVITY OF ANTITUMOR PROTEIN HYBRID (I)

A culture experiment was conducted with rat hepatoma cells AH 66 ($5\times10^4$) with the addition of the antitumor protein hybrid (final concentration: 5.2 μg/ml or 52 μg/ml) which was prepared in the preceding (c) in 1 ml of Eagle's MEM medium containing 10% fetal calf serum at 37° C. for 42 hours in an atmosphere of 5% carbon dioxide. A control experiment was also made with the use of 0.9% sodium chloride in place of the hybrid. Each experiment group consisted of three rows.

Figure 3:
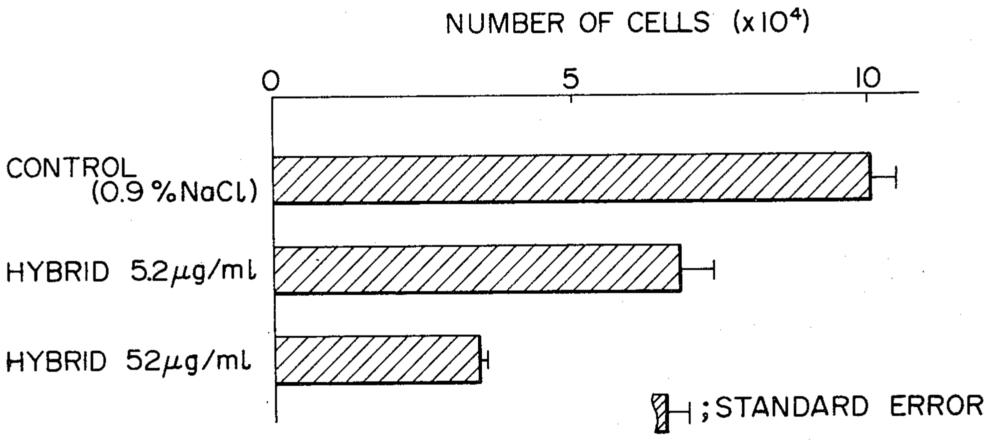
FIGS. 3 to 5 show the antitumor activity against AH 66 of the hybrid of the present invention prepared with the use of anti-AH 66 immunoglobulin.

After the culture was over, the cells were treated with saline buffered with phosphate containing 0.02% ethylenediaminetetraacetic acid to make homogenous cell suspensions and were then subjected to 0.3% Trypan Blue staining to determine the number of the viable cells under the microscope. The result is shown in FIG. 3, which indicates that, while the cells of the control group increased to $10.1\times10^4$, in the group to which the hybrid (5.2 μg/ml) was added the proliferation was subdued by approximately 60%, and in the group to which the hybrid (52 μg/ml) was added the proliferation was inhibited to perfection. This fact ascertains that the hybrid prepared according to the present invention has antitumor activity.

(e) ANTITUMOR ACTIVITY OF ANTITUMOR PROTEIN HYBRID (II)

A culture experiment was conducted with rat hepatoma cells AH 66 ($4.5\times10^4$) with the addition of the antitumor protein hybrid (final concentration: 0.1, 1, 10 or 100 μg/ml) prepared in the foregoing (c) or anti-AH 66 immunoglobulin IgG (final concentration: 1, 10 or 100 μg/ml) in 1 ml of Eagle's MEM medium containing 10% fetal calf serum at 37° C. for 48 hours in an atmosphere of 5% carbon dioxide. A control experiment was also made with the addition of 0.9% sodium chloride. Each experiment group consisted of three rows. After the culture was over, the treatment was made in accordance with the preceding (d).

Figure 4:
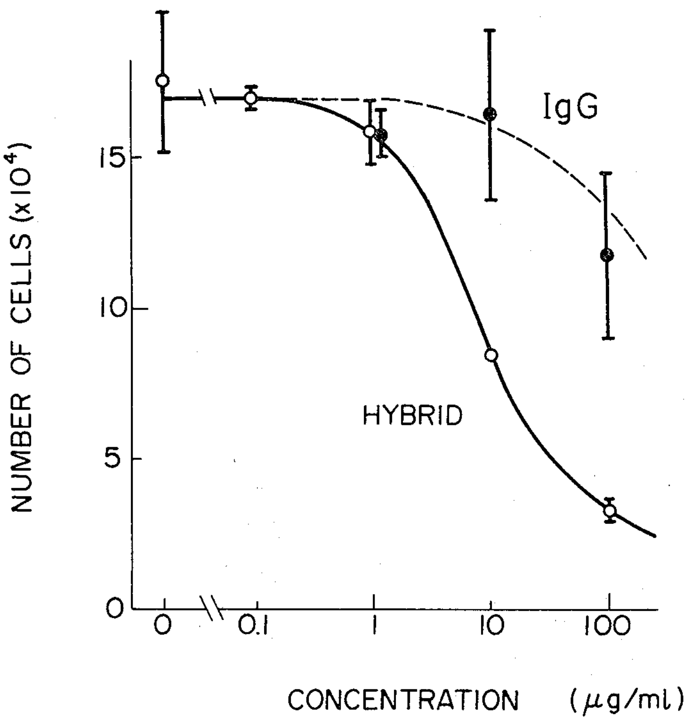

The result is shown in FIG. 4. It is made clear that the proliferation of the AH 66 cells was subdued more effectively as the concentration was higher in both cases of IgG and hybrid, but the hybrid had far better effect. Accordingly, this fact shows that the inhibitive effect of the hybrid on the proliferation of cells is based not on the function of the antibody but on the activity of the fragment A of a diphtheria toxin to inhibit the protein synthesis.

(f) ANTITUMOR ACTIVITY OF ANTITUMOR PROTEIN HYBRID (III)

A culture experiment was conducted with rat hepatoma cells AH 66 ($4.3\times10^4$) with the addition of the antitumor protein hybrid (final concentration: 10 or 100 μg/ml) prepared in the foregoing (c) in 1 ml of Eagle's MEM medium containing 10% calf serum at 37° C. for 1, 2, 3 or 4 days respectively in an atmosphere of 5% carbon dioxide. A control experiment was also made with the addition of 0.9% sodium chloride. Each experiment group consisted of three rows. The treatment after the culture was made in accordance with the foregoing (d).

Figure 5:
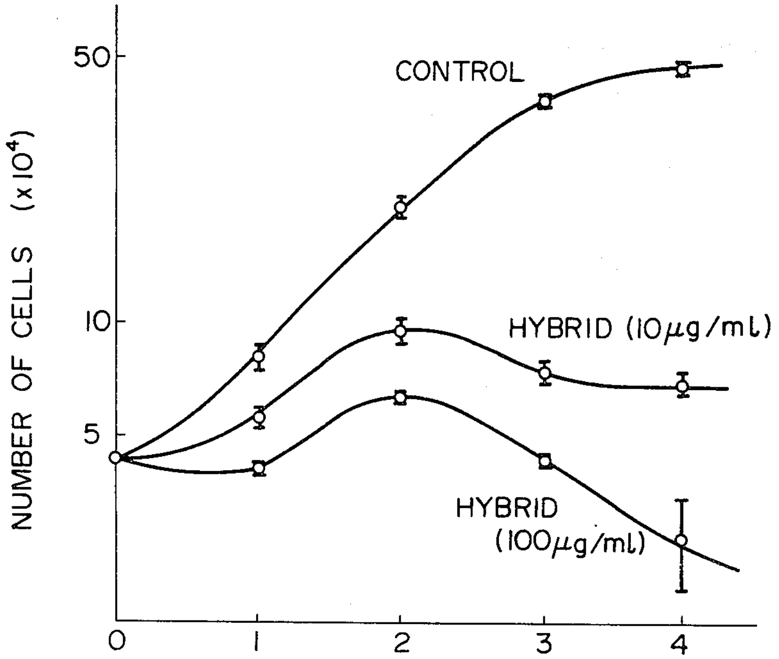

The result is shown in FIG. 5. A marked inhibitive effect on the proliferation of the cells was seen with the respective groups of different concentrations and the effect was especially remarkable on the third and fourth days of the experiment. It was also confirmed that the protein hybrid had not only an inhibitive effect on the proliferation of the cells but also an cytotoxic activity which causes the death of the cells. Also with regard to the viable cells which could not be stained by Trypan Blue, it was observed under the microscope that those viable cells of the treated groups were morphologically changed in contrast to those of the control groups.

EXAMPLE 2

(a) PREPARATION OF RABBIT ANTI-RAT α-FETOPROTEIN ANTIBODY 45 ml of an antiserum was obtained from two rabbits hyperimmunized with rat α-fetoprotein (hereinafter referred to as "AFP"). After having been inactivated, the antiserum was diluted with 45 ml of saline buffered with 10 m M phosphate and was then applied to a column of AFP Sepharose (about 14 ml; AFP was linked to Sepharose 4B in an amount of 2.3 mg per 1 ml of gel by the bromcyan method). After the gel was washed thoroughly with 30 ml of saline buffered with 10 m M phosphate, 50 ml of 0.5 M sodium chloride, and further with 100 ml of water, the anti-AFP antibody was eluted with hydrochloric acid (pH 2.8). Immediately after the elution, the eluate had its pH value raised by addition of (1/10) part by volume of 0.5 M Tris.HCl buffer (pH 8.3), was then concentrated by ultrafiltration, and was thoroughly dialized against 0.9% aqueous sodium chloride solution. The anti-AFP antibody thus obtained was found to be homogenous by SDS-polyacrylamide gel electrophoresis.

(b) PREPARATION OF ANTITUMOR PROTEIN HYBRID

Antitumor protein hybrid (in which one fragment A of diphtheria toxin in average was liked to one molecule of immunoglobulin) was obtained according to the same procedure of Example 1, (c), wherein the anti-AFP immunoglobulin obtained in the preceding (a) was used in the place of the anti-AH 66 immunoglobulin of Example 1, (c). When this hybrid was subjected to gel precipitation reaction against horse anti-diphtheria toxin antiserum and sheep anti-rabbit IgG antiserum, precipitin lines were formed in respective cases and these precipitin lines united together, from which it was confirmed that the hybrid was an antibody-toxin hybrid.

(c) ANTITUMOR ACTIVITY OF ANTITUMOR PROTEIN HYBRID

The activity was examined according to the same procedure taken in Example 1, (d), wherein the antitumor protein hybrid (final concentration: 11 or 110 μg/ml) prepared in the preceding (b) was added to rat hepatoma cells AH 66 ($5\times10^4$).

Figure 6:
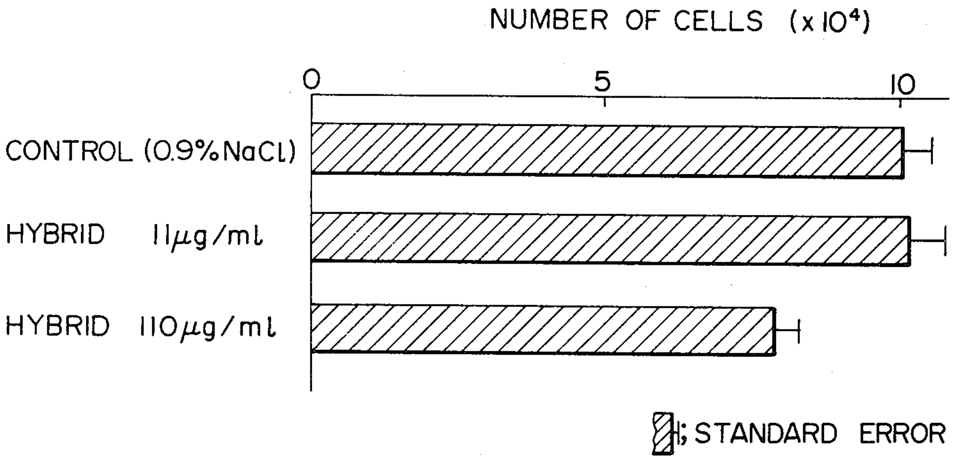
FIG. 6 shows the antitumor activity against AH 66 of the hybrid prepared with the use of anti-AFP immunoglobulin.

The result is shown in FIG. 6. In the experiment group where the hybrid was used at a concentration of 11 μg/ml, the cells proliferated quite as same as the control group, while in the group where the hybrid was used at a concentration of 110 μg/ml, the hybrid had about 40% inhibitive effect on the proliferation of the cells. It is, therefore, confirmed that the hybrid prepared with the use of an antibody against AFP, which is a foetal tumor antigen, has the antitumor activity similar to a hybrid prepared with the use of an anti-AH 66 antibody, though somewhat less potent.

What is claimed is:

1. Antitumor protein hybrid, having a moiety consisting of the antitumor immunoglobulin and a moiety substantially consisting of the fragment A of a diphtheria toxin, which is expressed by the following formula (I):

$$Ab\text{-}(NHCO-X-S_1-S_2-FA)_n \qquad (I)$$

where Ab indicates a moiety consisting of the antitumor immunoglobulin and FA indicates a moiety substantially consisting of the fragment A of a diphtheria toxin; X is an alkylene group or phenylene group which either has or does not have a branch chain of 1 to 5 carbon atoms; N in the amido bond is a nitrogen atom arising from the amino group in the antitumor immunoglobulin; $S_1$ and $S_2$ are both sulfur atoms, $S_2$ indicating a sulfur atom arising from the disulfide bond in a diphtheria toxin; n stands for an integer of 1 to 5.

2. Antitumor protein hybrid according to claim 1, wherein X is an ethylene group.

3. Antitumor protein hybrid according to claim 1, wherein FA is a moiety consisting of the fragment A of a diphtheria toxin.

4. A process for the preparation of antitumor protein hybrid expressed by the following formula (I), $$Ab(NHCO-X-S_1-S_2-FA)_n \quad (I)$$

where definitions of Ab, FA, X, N, $S_1$, $S_2$, and n are as same as those given in claim 1, which comprises reacting 1 to 5 amino groups of the antitumor immunoglobulin with a compound which is expressed by the following formula (II),

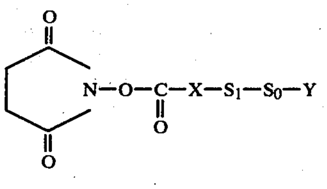

(II)

where X is an alkylene group or phenylene group which either has or does not have a branch chain of 1 to 5 carbon atoms, Y represents

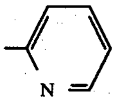

or

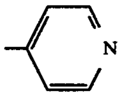

both $S_1$ and $S_0$ indicate a sulfur atom, and reacting the thus obtained product with the substantial fragment A of a diphtheria toxin which has at least one thiol group in the fragment.

* * * * *